United States Patent
Surmeier, Jr. et al.

(10) Patent No.: US 11,246,871 B2
(45) Date of Patent: Feb. 15, 2022

(54) TARGETING ADENOSINE A2A RECEPTORS FOR THE TREATMENT OF LEVODOPA-INDUCED DYSKINESIAS

(71) Applicant: Northwestern University, Evanston, IL (US)

(72) Inventors: Dalton James Surmeier, Jr., Chicago, IL (US); Weixing Shen, Wilmette, IL (US)

(73) Assignee: Northwestern University, Evanston, IL (US)

( * ) Notice: Subject to any disclaimer, the term of this patent is extended or adjusted under 35 U.S.C. 154(b) by 236 days.

(21) Appl. No.: 16/318,067

(22) PCT Filed: Jul. 14, 2017

(86) PCT No.: PCT/US2017/042178
§ 371 (c)(1),
(2) Date: Jan. 15, 2019

(87) PCT Pub. No.: WO2018/013951
PCT Pub. Date: Jan. 18, 2018

(65) Prior Publication Data
US 2020/0316074 A1    Oct. 8, 2020

Related U.S. Application Data

(60) Provisional application No. 62/362,937, filed on Jul. 15, 2016.

(51) Int. Cl.
*A61K 31/522* (2006.01)
*A61P 25/14* (2006.01)
(Continued)

(52) U.S. Cl.
CPC .......... *A61K 31/522* (2013.01); *A61K 31/198* (2013.01); *A61K 45/06* (2013.01); *A61P 25/14* (2018.01); *A61P 25/28* (2018.01)

(58) Field of Classification Search
CPC .. A61K 31/522; A61K 31/198; A61K 31/519; A61K 31/5377; A61K 45/06; A61P 25/14; A61P 25/28; A61P 25/16
(Continued)

(56) References Cited

U.S. PATENT DOCUMENTS

| 4,657,760 A | 4/1987 | Kung et al. |
| 5,206,344 A | 4/1993 | Katre et al. |

(Continued)

FOREIGN PATENT DOCUMENTS

| WO | WO 2004/097009 | 11/2004 |
| WO | WO 2005/075465 | 8/2005 |
| WO | WO 2012/060844 | 5/2012 |

OTHER PUBLICATIONS

Bateup, H. S. et al. Distinct subclasses of medium spiny neurons differentially regulate striatal motor behaviors. Proc Natl Acad Sci U S A. Aug. 17, 2010;107(33):14845-50.

(Continued)

*Primary Examiner* — Taylor V Oh
(74) *Attorney, Agent, or Firm* — Casimir Jones SC; David W. Staple

(57) ABSTRACT

Provided herein are compositions and methods for the treatment and of neurodegenerative disorders and levodopa-induced dyskinesias. In particular, A2a receptor antagonists are provided, as well as methods for the use of A2a receptor antagonists in the treatment of neurodegenerative disorders (e.g., Parkinsons disease) and the treatment and/or prevention levodopa-induced dyskinesias associated with such treatment.

9 Claims, 4 Drawing Sheets

(51) Int. Cl.
*A61P 25/28* (2006.01)
*A61K 31/198* (2006.01)
*A61K 45/06* (2006.01)

(58) Field of Classification Search
USPC .......................................... 514/263, 263.36
See application file for complete search history.

(56) References Cited

U.S. PATENT DOCUMENTS

| | | |
|---|---|---|
| 5,225,212 A | 7/1993 | Martin et al. |
| 5,945,424 A | 8/1999 | Schmidt |
| 2008/0176858 A1 | 7/2008 | Beauglehole et al. |
| 2009/0029967 A1 | 1/2009 | Grzelak et al. |
| 2014/0249166 A1 | 9/2014 | Kase et al. |

OTHER PUBLICATIONS

Calon, F. et al. Increased adenosine A2A receptors in the brain of Parkinson's disease patients with dyskinesias. Brain. May 2004;127(Pt 5):1075-84.

Chen, W., et al. Istradefylline, an adenosine A2A receptor antagonist, for patients with Parkinson's Disease: a meta-analysis. Neurol Res. Nov. 2014;36(11):1028-34.

De Lau, L. M. L. et al. Incidence of parkinsonism and Parkinson disease in a general population: the Rotterdam Study. Neurology. Oct. 12, 2004;63(7):1240-4.

Fahn, S. The history of dopamine and levodopa in the treatment of Parkinson's disease. Mov Disord. 2008;23 Suppl 3:S497-508.

Fernandez, H. H. et al. Istradefylline as monotherapy for Parkinson disease: results of the 6002-US-051 trial. Parkinsonism Relat Disord. Jan. 2010;16(1):16-20.

Findley, L. J. The economic impact of Parkinson's disease. Parkinsonism Relat Disord. Sep. 2007;13 Suppl:S8-S12.

Fino, E., et al. Bidirectional activity-dependent plasticity at corticostriatal synapses. J Neurosci. Dec. 7, 2005;25(49):11279-87.

Gerfen, C. R. et al. Modulation of striatal projection systems by dopamine. Annu Rev Neurosci. 2011;34:441-66.

Hauser, R. A. et al. Preladenant in patients with Parkinson's disease and motor fluctuations: a phase 2, double-blind, randomised trial. Lancet Neurol. Mar. 2011;10(3):221-9.

Hauser, R. A. et al. Tozadenant (SYN115) in patients with Parkinson's disease who have motor fluctuations on levodopa: a phase 2b, double-blind, randomised trial. Lancet Neurol. Aug. 2014;13(8):767-76.

Hornykiewicz, O. Dopamine (3-hydroxytyramine) and brain function. Pharmacol Rev. Jun. 1966;18(2):925-64.

Huot, P.,et al. The pharmacology of L-DOPA-induced dyskinesia in Parkinson's disease. Pharmacol Rev. Jan. 10, 2013;65(1):171-222.

Jia, Y., et al. Presynaptic BDNF promotes postsynaptic long-term potentiation in the dorsal striatum. J Neurosci. Oct. 27, 2010;30(43):14440-5.

Kerr, J. N. et al. Dopamine D-1/D-5 receptor activation is required for long-term potentiation in the rat neostriatum in vitro. J Neurophysiol. Jan. 2001;85(1):117-24.

Kish, S. J., et al. Uneven pattern of dopamine loss in the striatum of patients with idiopathic Parkinson's disease. Pathophysiologic and clinical implications. N Engl J Med. Apr. 7, 1988;318(14):876-80.

Kondo, T., et al. Japanese Istradefylline Study Group. A long-term study of istradefylline safety and efficacy in patients with Parkinson disease. Clin Neuropharmacol. Mar.-Apr. 2015;38(2):41-6.

Kreitzer, A. C. et al. Striatal plasticity and basal ganglia circuit function. Neuron. Nov. 26, 2008;60(4):543-54.

Lerner, T. N. et al. RGS4 is required for dopaminergic control of striatal LTD and susceptibility to parkinsonian motor deficits. Neuron. Jan. 26, 2012;73(2):347-59.

Lerner, T. N., et al. Endocannabinoid signaling mediates psychomotor activation by adenosine A2A antagonists. J Neurosci. Feb. 10, 2010;30(6):2160-4.

Lewitt, P. A. et al. Adenosine A2A receptor antagonist istradefylline (KW-6002) reduces 'off' time in Parkinson's disease: a double-blind, randomized, multicenter clinical trial (6002-US-005). Ann Neurol. Mar. 2008;63(3):295-302.

Lundbad, M., Cellular and behavioural effects of the adenosine A2a receptor antagonist KW-6002 in a rat model of l-DOPA-induced dyskinesia. J Neurochem. Mar. 2003;84(6):1398-410.

Mishina, M. et al. Adenosine A(2A) receptors measured with [C]TMSX PET in the striata of Parkinson's disease patients. PLoS One. Feb. 28, 2011;6(2):e17338.

Mizuno, Y. et al. Clinical efficacy of istradefylline (KW-6002) in Parkinson's disease: a randomized, controlled study. Mov Disord. Jul. 30, 2010;25(10):1437-43.

Park, A. et al. Istradefylline for the treatment of Parkinson's disease. Expert Opin Pharmacother. Jan. 2012;13(1):111-4.

Park, H., et al. Essential role of presynaptic NMDA receptors in activity-dependent BDNF secretion and corticostriatal LTP. Neuron. Dec. 3, 2014;84(5):1009-22.

Pascoli, V., et al. Reversal of cocaine-evoked synaptic potentiation resets drug-induced adaptive behaviour. Nature. Dec. 7, 2011;481(7379):71-5.

Pawlak, V. et al. Dopamine receptor activation is required for corticostriatal spike-timing-dependent plasticity. J Neurosci. Mar. 5, 2008;28(10):2435-46.

Picconi, B. et al. Loss of bidirectional striatal synaptic plasticity in L-DOPA-induced dyskinesia. Nat Neurosci. May 2003;6(5):501-6.

Plotkin, J. L. et al. Impaired TrkB receptor signaling underlies corticostriatal dysfunction in Huntington's disease. Neuron. Jul. 2, 2014;83(1):178-88.

Shen, W. et al. M4 muscarinic receptor signaling ameliorates striatal plasticity deficits in models of L-DOPA-induced dyskinesia. Neuron. Jun. 1, 2016;90(5):1139.

Shen, W., et al. Dichotomous dopaminergic control of striatal synaptic plasticity. Science. Aug. 8, 2008;321(5890):848-51.

Tomiyama, M. et al. Upregulation of striatal adenosine A2A receptor mRNA in 6-hydroxydopamine-lesioned rats intermittently treated with L-DOPA. Synapse. Jun. 1, 2004;52(3):218-22.

Yagishita, S. et al. A critical time window for dopamine actions on the structural plasticity of dendritic spines. Science. Sep. 26, 2014;345(6204):1616-20.

TARGETING ADENOSINE A2A RECEPTORS FOR THE TREATMENT OF LEVODOPA-INDUCED DYSKINESIAS

CROSS-REFERENCE TO RELATED APPLICATION

The present application claims priority to U.S. Provisional Patent Application Ser. No. 62/362,937 filed Jul. 15, 2016, which is hereby incorporated by reference in its entirety.

STATEMENT REGARDING FEDERAL FUNDING

This invention was made with government support under R01 NS034696 awarded by the National Institutes of Health. The government has certain rights in the invention.

FIELD

Provided herein are compositions and methods for the treatment and of neurodegenerative disorders and levodopa-induced dyskinesias. In particular, A2a receptor antagonists are provided, as well as methods for the use of A2a receptor antagonists in the treatment of neurodegenerative disorders (e.g., Parkinson's disease) and the treatment and/or prevention levodopa-induced dyskinesias associated with such treatment.

BACKGROUND

Parkinson's disease (PD) is the second most common neurodegenerative disorder. The core motor symptoms are caused by the loss of midbrain dopamine (DA) neurons. Levodopa, a DA precursor, provides the most effective symptomatic treatment by elevating DA release from residual neurons. However, chronic levodopa administration at concentrations sufficient to achieve symptomatic relief, particularly in late stage PD patients or those on long-term levodopa treatment, leads to the emergence of disabling motor side effects, termed levodopa-induced dyskinesia (LID). There is a critical need for a pharmacotherapy to alleviate LID without surgery.

SUMMARY

Provided herein are compositions and methods for the treatment and of neurodegenerative disorders and levodopa-induced dyskinesias. In particular, A2a receptor antagonists are provided, as well as methods for the use of A2a receptor antagonists in the treatment of neurodegenerative disorders (e.g., Parkinson's disease) and the treatment and/or prevention levodopa-induced dyskinesias associated with such treatment.

In some embodiments, provided herein are methods for the treatment of a neurodegenerative disorder without inducing dyskinesia (or with reduced dyskinesia (e.g., levodopa-induced dyskinesia)), comprising: (a) administering to a subject a dose of levodopa at a first time-point; (b) administering to the subject a dose of an A2a antagonist at a second time-point following a time delay from the first time point.

In some embodiments, provided herein are methods for the treatment of a neurodegenerative disorder with reduced levodopa-induced dykinesia, comprising administering to the subject a dose of an A2a antagonist at a time when plasma levodopa levels are low (e.g., in the morning, hours after L-DOPA administration, at or near the trough or valley of plasma levodopa levels).

In some embodiments, the neurodegenerative disorder is Parkinson's disease. In some embodiments, the A2a antagonist is selected form the group consisting of: ATL-444, Istradefylline (KW-6002), MSX-3, Preladenant (SCH-420,814), SCH-58261, SCH-412,348, SCH-442,416, ST-1535, caffeine, VER-6623, VER-6947, VER-7835, Vipadenant (BIIB-014), ZM-241,385, Tozadenant, V81444 and CPI-444. In some embodiments, the time delay is at least 1 hour (e.g., 1 hour, 2 hours, 3 hours, 4 hours, 5 hours, 6 hours, 7 hours, 8 hours, or more, or ranges therebetween). In some embodiments, the second time-point is after symptom-reduction effects of the dose of levodopa have begun to decrease (e.g., upon the return of symptoms).

In some embodiments, methods further comprise co-administering an additional therapeutic agent for the treatment of the neurodegenerative disorder or symptom reduction. In some embodiments, the additional therapeutic agent is selected from the list consisting of dopamine agonists (e.g., bromocriptine, pergolide, pramipexole, ropinirole, piribedil, cabergoline, apomorphine, lisuride, etc.), MAO-B inhibitors (e.g., selegiline, rasagiline, etc.), and other therapeutics, such as amantadine, anticholinergics, quetiapine, cholinesterase inhibitors, modafinil, non-steroidal anti-inflammatory drugs, etc. In some embodiments, the additional therapeutic agent is administered at the first time-point. In some embodiments, the additional therapeutic agent is co-formulated with the levodopa. In some embodiments, the additional therapeutic agent is separately-formulated from the levodopa. In some embodiments, the additional therapeutic agent is administered at the second time-point. In some embodiments, the additional therapeutic agent is co-formulated with the A2a antagonist. In some embodiments, the additional therapeutic agent is separately-formulated from the A2a antagonist. In some embodiments, the additional therapeutic agent is administered between the first time-point and the second time-point.

In some embodiments, provided herein are kits (e.g., for the treatment of PD with reduced LID) comprising: (a) levodopa; (b) an A2a antagonist; and (c) instructions to administer the levodopa first, and the A2a antagonist second, after a time delay. In some embodiments, the A2a antagonist is selected form the group consisting of: ATL-444, Istradefylline (KW-6002), MSX-3, Preladenant (SCH-420,814), SCH-58261, SCH-412,348, SCH-442,416, ST-1535, caffeine, VER-6623, VER-6947, VER-7835, Vipadenant (BIIB-014), ZM-241,385, Tozadenant, V81444 and CPI-444. In some embodiments, the time delay indicated by the instructions is at least 1 hour (e.g., 1 hour, 2 hours, 3 hours, 4 hours, 5 hours, 6 hours, 7 hours, 8 hours, or more, or ranges therebetween). In some embodiments, the instructions indicate that the A2a antagonist is to be administered is after symptom-reduction effects of the levodopa have begun to decrease. In some embodiments, the levodopa and the A2a antagonist are contained in separate containers. In some embodiments, the separate containers are packaged together.

In some embodiments, kits further comprise an additional therapeutic agent. In some embodiments, the additional therapeutic agent is selected from the list consisting of dopamine agonists (e.g., bromocriptine, pergolide, pramipexole, ropinirole, piribedil, cabergoline, apomorphine, lisuride, etc.), MAO-B inhibitors (e.g., selegiline, rasagiline, etc.), and other therapeutics, such as amantadine, anticholinergics, quetiapine, cholinesterase inhibitors, modafinil, non-steroidal anti-inflammatory drugs, etc. In some embodiments, the instructions indicate that additional therapeutic agent is to be administered concurrently with the levodopa. In some embodiments, the additional therapeutic agent is co-formulated with the levodopa. In some embodiments, the additional therapeutic agent is separately-formulated from the levodopa. In some embodiments, the instructions indicate that additional therapeutic agent is to be administered concurrently with the A2a antagonsit. In some embodiments, the additional therapeutic agent is co-formulated with the A2a antagonist. In some embodiments, the additional therapeutic agent is separately-formulated from the A2a antagonist. In some embodiments, the instructions indicate that additional therapeutic agent is to be administered between the first time-point and the second time-point.

DEFINITIONS

Figure 1:
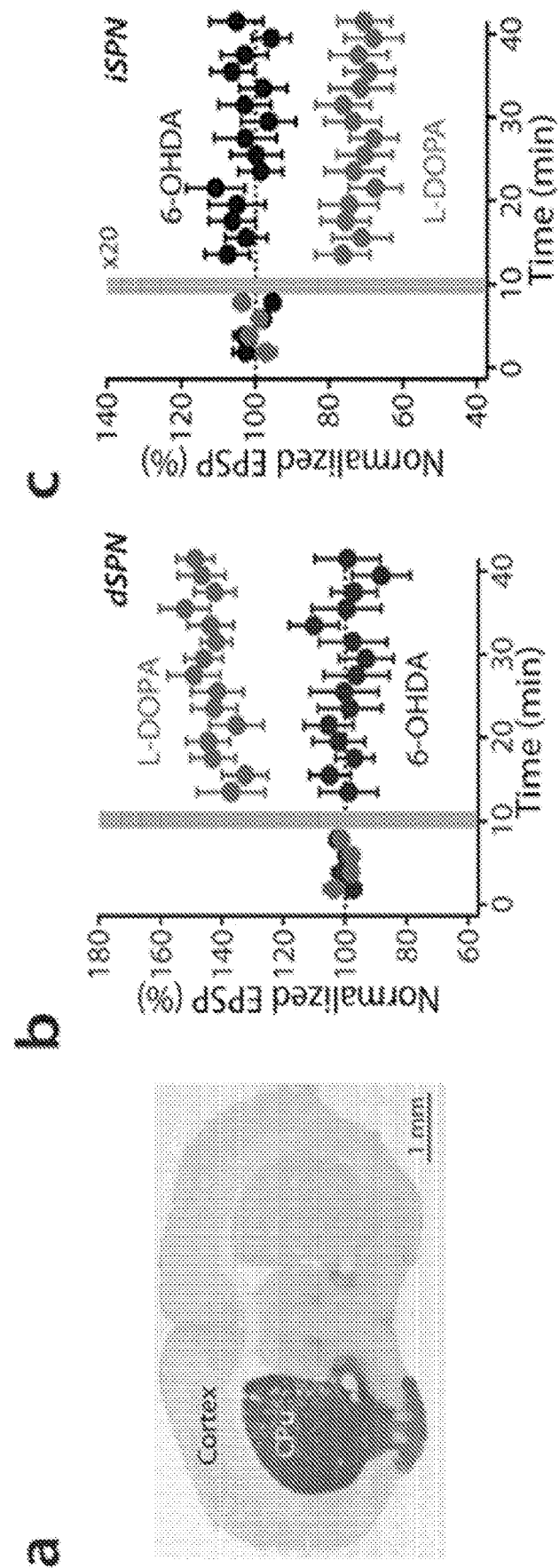
FIG. 1. SPN synaptic plasticity during the expression of LID. a) Light microscopic image of a coronal section illustrating the loss of immunoreactivity for tyrosine hydroxylase after unilateral MFB 6-OHDA lesioning. CPu, caudate-putamen. b) LTP induction was lost in prolonged lesioned animals. Shortly after the lase injection of L-DOPA, LTP was recovered in dSPNs. c) iSPN LTD induction was lost in lesioned animals. LTD was recovered in the dyskinetic ON-state.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an A2a receptor antagonist" is a reference to one or more A2a receptor antagonists, unless the context clearly dictates otherwise.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., an A2a antagonist, levodopa, and/or additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are compositions and methods for the treatment and of neurodegenerative disorders and levodopa-induced dyskinesias. In particular, A2a receptor antagonists are provided, as well as methods for the use of A2a receptor antagonists in the treatment of neurodegenerative disorders (e.g., Parkinson's disease) and the treatment and/or prevention levodopa-induced dyskinesias associated with such treatment.

Levodopa (L-DOPA) or L-3,4-dihydroxyphenylalanine: is a chemical that is made and used as part of the normal biology of humans, some animals and plants. L-DOPA is the precursor to the neurotransmitters dopamine, norepinephrine (noradrenaline), and epinephrine (adrenaline) collectively known as catecholamines. L-DOPA mediates neurotrophic factor release by the brain and CNS. L-DOPA is manufactured and sold as a psychoactive drug under trade names including SINEMET, PHARMACOPA, ATAMET, STALEVO, MADOPAR, and PROLOPA. Levodopa is prescribed and administered for the treatment of neurodegenerative disorders, and in particular in the clinical treatment of Parkinson's disease and dopamine-responsive dystonia.

Levodopa is typically provided orally, and is initially administered to a subject at a dose of 200-600 mg (e.g., 200 mg, 250 mg, 300 mg, 350 mg, 400 mg, 450 mg, 500 mg, 550 mg, 600 mg, or ranges therebetween (e.g., 250-500 mg, etc.)) orally twice a day with meals. With use of levodopa, dosages are typically increased over time. Maintenance doses of 2000 to 7000 mg/day (e.g., 2000, 2500, 3000, 3500, 4000, 4500, 5000, 5500, 6000, 6500, 7000, or ranges therebetween (e.g., 3000-6000 mg/day)) divided into three separate doses (e.g., not to exceed 8000 mg/day) are commonly administered.

Unfortunately, levodopa administration at the above concentrations (e.g., concentrations sufficient to achieve symptomatic relief, particularly in late stage PD patients) leads to the emergence of disabling motor side effects, termed levodopa-induced dyskinesia (LID). LID is characterized by hyperkinetic movements, including chorea (e.g., involuntary, rapid, irregular, purposeless, and unsustained movements that seem to flow from one body part to another), dystonia (e.g., sustained muscle contractions), and athetosis (e.g., involuntary writhing movements associated with abnormal muscle contractions). LIDs are classified based on their relationship with, and timing related to, levodopa dosing. Peak-dose dyskinesias are the most common forms of LID and are related to peak plasma levels of levodopa. They involve the head, trunk, and limbs, and sometimes respiratory muscles. Levodopa dose reduction can ameliorate them, frequently at the cost of deterioration of Parkinsonism. Diphasic dyskinesias develop when plasma levodopa levels are rising or falling. They are also called D-I-D (dyskinesia-improvement-dyskinesia). They do not respond to levodopa dose reduction and may improve with high dose of levodopa. Off-state dystonias occur when plasma levodopa levels are low (e.g., in the morning, several hours after L-DOPA dosing (e.g., 2, 3, 4, 5, 6, 7, 8, 9 10, 11, 12 hours).

The adenosine A2a receptor, also known as ADORA2A, is an G-protein couple receptor that is believed to play a role in regulating myocardial oxygen consumption, coronary blood flow, and can negatively regulate overreactive immune cells, thereby protecting tissues from collateral inflammatory damage. Antagonists of the A2a receptor have been proposed as treatment for PD. Studies using A2a receptor antagonists as a potential treatment for LID have yielded negative results.

In some embodiments, provided herein are methods (e.g., dosing regimens) of co-administering levodopa and an A2a antagonist for the treatment of PD with reduced LID side effects (e.g., as compared to L-DOPA administration alone, compared to other dosing regimens using L-DOPA and an A2a antagonist, etc.). In some embodiments, methods herein treat, prevent, or reduce LID, off-state dystonias, diphasic dyskinesias, peak-dose dyskinesias. In some embodiments, methods herein treat PD and/or reduce symptoms associated thrrewith.

In some embodiments, the A2a antagonist is not administered concurrently or simultaneously with the levodopa. In some embodiments, an A2a antagonist is administered when plasma levodopa levels are low (e.g., below 1 mg/liter (e.g., 0.9 mg/l, 0.8 mg/l, 0.7 mg/l, 0.6 mg/l, 0.5 mg/l, 0.4 mg/l, 0.3 mg/l, 0.2 mg/l, 0.1 mg/l, <0.1 mg/l, or ranges therebetween). In some embodiments, an A2a antagonist is administered when plasma levodopa levels are less than 75% (e.g., 75%, 70%, 65%, 60%, 55%, 50%, 45%, 40%, 35%, 30%, 25%, 20%, 15%, 10%, 5%, 1%, or less, or ranges therebetween) of peak plasma levodopa levels. In some embodiments, an A2a antagonist is administered when symptom reduction associated with administration of a levodopa dose is waning (e.g., symptoms are beginning to return). In some embodiments, an A2a antagonist is administered when LID symptoms are returning (e.g., off-state symptoms) following administration of a levodopa dose. In some embodiments, an A2a antagonist is administered 1-24 hours (e.g., 1, 2, 3, 4, 5, 6, 7, 8, 9, 10, 11, 12, 13, 14, 15, 16, 17, 18, 19, 20, 21, 22, 23, 24, or ranges therebetween (e.g., 3-12 hours, 4-8 hours, etc.)) following administration of a levodopa dose.

In some embodiments, a levodopa dose is not administered concurrently or simultaneously or concurrently with an A2a antagonist. In some embodiments, a time delay is provided between administration of an A2a antagonist and a subsequent levodopa dose. In some embodiments, the time delay is at least 30 minutes (e.g., 30 minutes, 45 minutes, 60 minutes, 75 minutes, 90 minutes, 105 minutes, 120 minutes, 150 minutes, 180 minutes, 210 minutes, 240 minutes, or more, or ranges therebetween). In some embodiments, the time delay is at 11-12 hours (e.g., 1 hour, 2 hours, 3 hours, 4 hours, 5 hours, 6 hours, 7 hours, 8 hours, 9 hours, 10 hours, 11 hours, 12 hours, or ranges therebetween).

An exemplary dosing regimen for the co-administration of levodopa and an A2a antagonist for the treatment of PD with the reduction of LID comprises: first levodopa dose—first time delay—A2a antagonist dose—second time delay—second levodopa dose. In some embodiments, a dose of A2a antagonist is administered in the morning, following the break from levodopa administration provided by sleep. In such emboidments, an exemplary regimen may include: morning A2a antagonist dose-time delay—levodopa dose. This regimen may be followed by additional delays and doses of levodopa and/or A2a antagonist.

In some embodiments, any suitable A2a antagonists may find use in embodiments herein. Exemplary A2a antagonists include, but are not limited to:

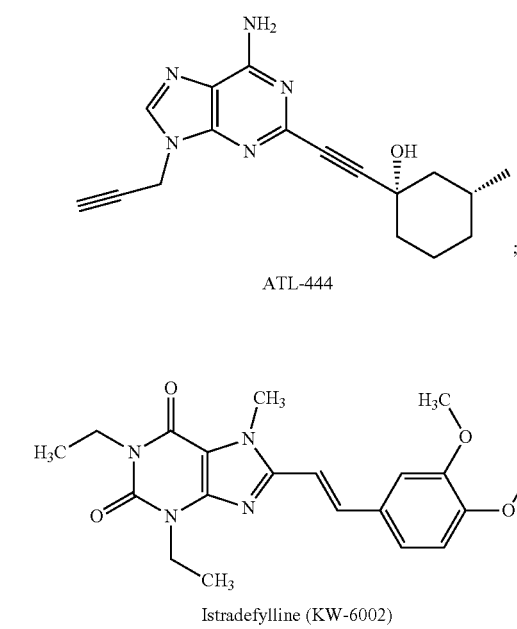

ATL-444

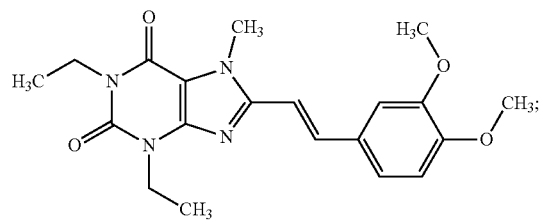

Istradefylline (KW-6002)

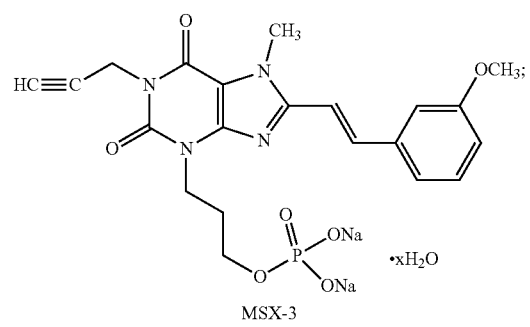

MSX-3

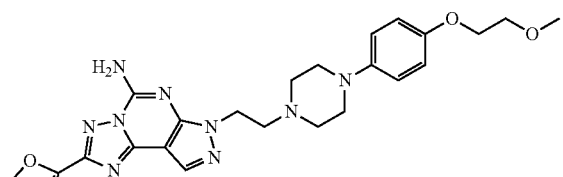

Preladenant (SCH-420,814)

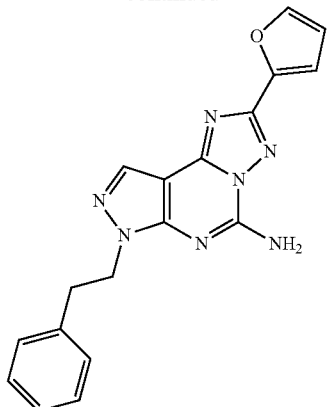

SCH-58261

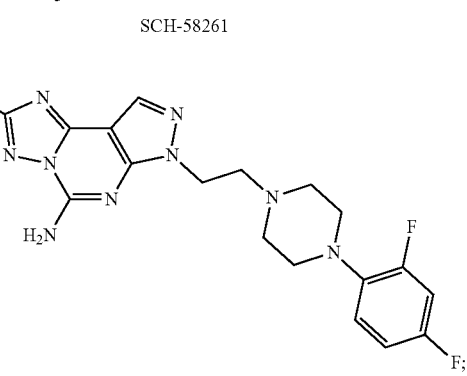

SCH-412,348

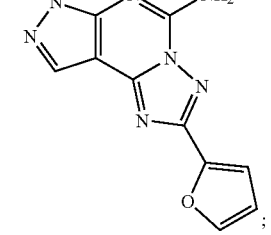

SCH-442,416

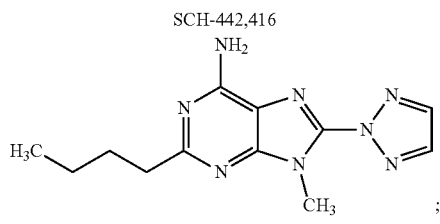

ST-1535

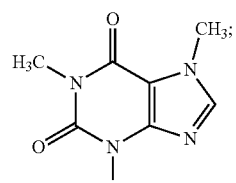

caffeine

-continued

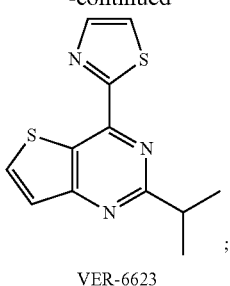

VER-6623

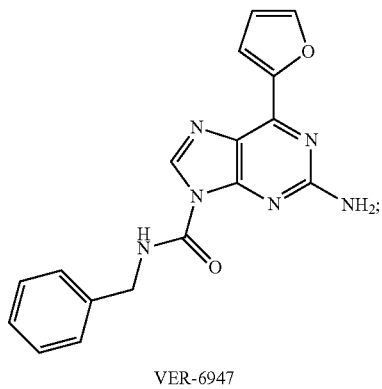

VER-6947

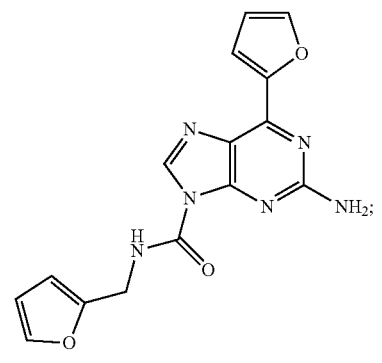

VER-7835

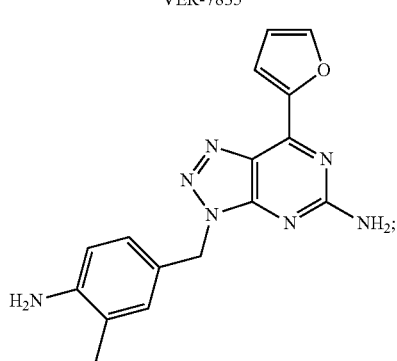

Vipadenant (BIIB-014)

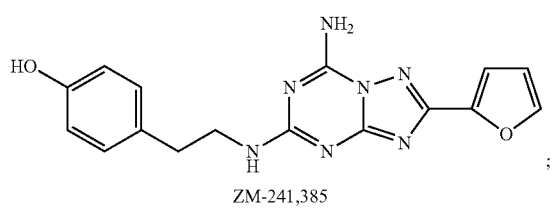

ZM-241,385

-continued

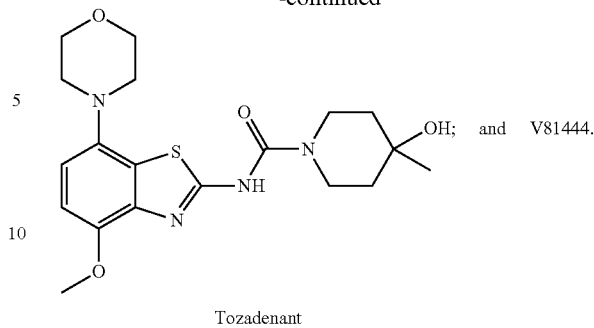

Tozadenant

Other A2a antagonists are within the scope of embodiments herein.

As is well known in the medical arts, dosages (e.g., levodopa dosages, A2a antagonist dosages, etc.) for any one patient depends upon many factors, including the patient's size, body surface area, age, the particular compound to be administered, sex, time and route of administration, general health, and interaction with other drugs being concurrently administered.

Pharmaceutical compositions herein may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, pharmaceutical compositions may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions are formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions include compositions wherein the active ingredients (e.g., A2a antagonist, levodopa, etc.) are contained in an effective amount to achieve the intended purpose. For example, an effective amount of therapeutic may be an amount that prevents levodopa-induced dyskinesias and/or treats or reduces symptoms associated with PD. Determination of effective amounts is well within the capability of those skilled in the art, especially in light of the disclosure provided herein.

In addition to the active therapeutic ingredients, pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions. The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (e.g., dosage).

Pharmaceutical preparations for oral administration include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Therapeutic compositions formulated in a pharmaceutical acceptable carrier may be prepared, placed in an appropriate container, and labeled for treatment of the indicated condition (e.g., levodopa-induced dyskinesias, PD, etc.).

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

In some embodiments, a therapeutically effective dose may be estimated initially from cell culture assays and/or animal models (particularly murine models). A therapeutically effective dose refers to that amount that effectively addresses and underlying cause and/or ameliorates symptoms of the disease state or unwanted condition (e.g., levodopa-induced dyskinesias, PD, etc.). Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. Data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration. The exact dosage is chosen by the individual clinician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Typical dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; 5,225,212; WO2004/097009, or WO2005/075465, each of which are herein incorporated by reference).

In some embodiments, the therapies disclosed herein are combined or used in combination with other agents useful in the treatment of psychomotor diseases (e.g., PD). Or, by way of example only, the therapeutic effectiveness of one of the therapies described herein may be enhanced by administration of an adjuvant (e.g., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In some embodiments, one or more of the therapies provided herein (e.g., A2a antagonist, levodopa, etc.) are combined with each other, and/or with one or more treatments for a psychomotor disease (e.g., PD). Suitable treatments for psychomotor disease (e.g., PD) for co-administration (e.g., with A2a antagonist, levodopa, etc.) include dopamine agonists (e.g., bromocriptine, pergolide, pramipexole, ropinirole, piribedil, cabergoline, apomorphine, lisuride, etc.), MAO-B inhibitors (e.g., selegiline, rasagiline, etc.), and other therapeutics, such as amantadine, anticholinergics, quetiapine, cholinesterase inhibitors, modafinil, non-steroidal anti-inflammatory drugs, etc.

In some embodiments, deep brain stimulation is also utilized for the treatment of PD, in addition to the other embodiments described herein.

In some embodiments, one or more therapeutic approaches described herein co-administered to a subject. In some embodiments, co-administration involves co-formulation of two or more agents together into the same medicament. In other embodiments, the agents are in separate formulations but are administered together, either simultaneously or in sequence (e.g., separated by one or more minutes, hours, days, etc.). In some embodiments, where a synergistic or additive benefit is achieved, the co-administered agent may be provided at a lower dose than would normally be administered if that agent were being used in isolation to treat the disease or condition.

The technology provided herein also includes kits for use in the instant methods. Kits of the technology comprise one or more containers comprising a therapeutic approach described herein and/or a second agent, and in some variations further comprise instructions for use in accordance with any of the methods provided herein. The kit may further comprise a description of selecting an individual suitable treatment. Instructions supplied in the kits of the technology are typically written instructions on a label or package insert (e.g., a paper insert included with the kit), but machine-readable instructions (e.g., instructions carried on a magnetic or optical storage disk) are also contemplated. In some embodiments, the kit is a package containing a sealed container comprising any one of the preparations described above, together with instructions for use. The kit can also include a diluent container containing a pharmaceutically acceptable diluent. The kit can further comprise instructions for mixing the preparation and the diluent. The diluent can be any pharmaceutically acceptable diluent. Well known diluents include 5% dextrose solution and physiological saline solution. The container can be an infusion bag, a sealed bottle, a vial, a vial with a septum, an ampoule, an ampoule with a septum, an infusion bag, or a syringe. The containers can optionally include indicia indicating that the containers have been autoclaved or otherwise subjected to sterilization techniques. The kit can include instructions for administering the various solutions contained in the containers to subjects.

EXPERIMENTAL

PD is the second most common aging-linked neurodegenerative disease in developed countries, afflicting nearly 1 million Americans at an estimated cost that exceeds $25 B/year (Refs 1,2; incorporated by reference in their entireties). The cardinal motor symptoms of the disease (bradykinesia and rigidity) are linked to the death of midbrain dopaminergic neurons innervating the striatum (Refs 3,4; incorporated by reference in their entireties). The primary symptomatic treatment for PD patients—administration of L-3,4-dihydroxyphenylalanine (L-DOPA) to boost dopamine (DA) release from remaining neurons—has not fundamentally changed for the past half-century (Ref. 5; incorporated by reference in its entirety). Although it is initially effective in alleviating motor symptoms, as the disease progresses, L-DOPA becomes less effective and dose required to achieve symptomatic benefit rises. In most patients, high doses of L-DOPA produce unwanted side-effects, most prominently, involuntary movements that manifest as dyskinesia (Ref. 6; incorporated by reference in its entirety). At present, short of deep brain stimulation of the subthalamic nucleus, there are no effective means of diminishing L-DOPA-induced dyskinesia (LID). As a consequence, there is a concerted effort to develop new and effective therapies for PD and LID.

The development of new symptomatic medications and adjunct therapies to ameliorate LID should come from a better understanding of how corticostriatal glutamatergic synaptic strength in striatal neurons is regulated in the LID state. Striatal principal spiny projection neurons (SPNs) can be divided into two major classes—the so-called direct pathway SPNs (dSPNs) project directly, whereas indirect pathway SPNs (iSPNs) project indirectly to the output structures of basal ganglia. Two forms of long-term synaptic plasticity have been described in SPNs. Long-term depression (LTD) of glutamatergic corticostriatal synapses is dependent upon retrograde endocannabinoid (eCB) signaling (Ref. 7,8; incorporated by reference in their entireties). eCB-mediated LTD is dependent upon type 5 metabotropic glutamate receptors (mGluR5) activation; it is also postsynaptically induced but presynaptically expressed. $G_i$-coupled DA D2 receptors (D2Rs)/muscarinic M4 receptors (M4Rs) are required to diminish protein kinase A (PKA) phosphorylation of regulator of G protein signaling 4 (RGS4), which negatively modulates mGluR5 stimulation of phospholipase C isoforms coupled to the generation of eCBs necessary for LTD induction (Refs. 9,10; incorporated by reference in their entireties).

Long-term potentiation (LTP) induction requires co-activation of NMDARs and $G_{olf}$-coupled DA D1 receptors (D1Rs)/adenosine A2a receptors (A2aRs) (Refs. 10-18; incorporated by reference in their entireties). Acting through PKA, D1R and A2aR activation leads to the phosphorylation of DA and cAMP-regulated phosphoprotein of 32 kDa (DARPP-32) and a variety of other downstream signaling molecules, including extracellular signal-regulated kinase (ERK), linked to synaptic plasticity (Refs. 10, 16-20; incorporated by reference in their entireties).

Figure 2:
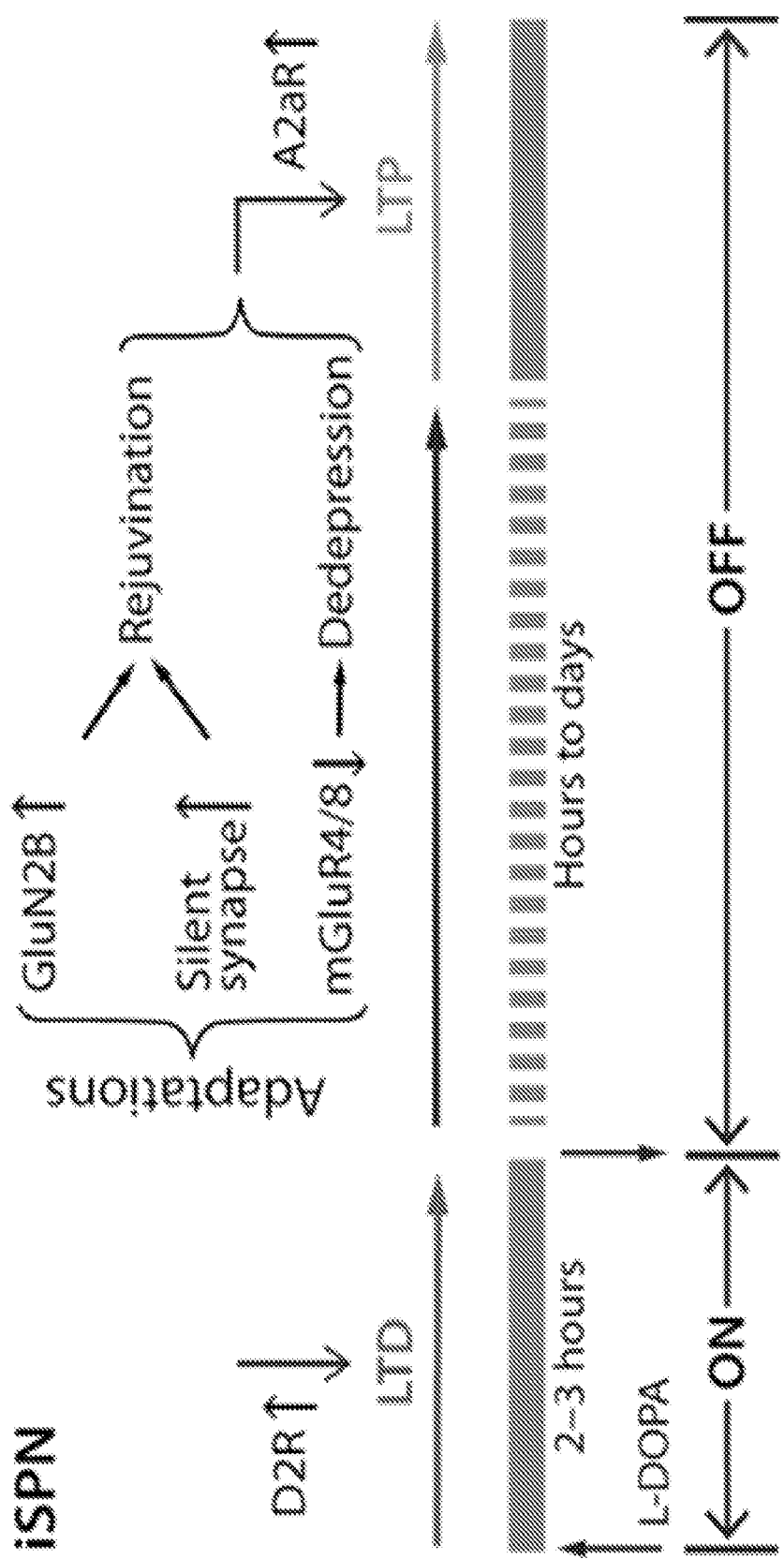
FIG. 2. L-DOPA induces iSPN synaptic adaptations including rejuvenation of glutamatergic synapses and de-depression of presynaptic mGuR4/8 receptors. Both helps promote iSPN LTP, contributing to the development of LID movements.

In PD models, striatal synaptic plasticity is lost (Refs. 10, 21; incorporated by reference in their entireties). Elevating striatal DA in lesioned animals by systemic administration of L-DOPA restores LTP in dSPNs and LTD in iSPNs (FIG. 1), indicating that synaptic plasticity is not grossly abnormal and continues to be governed by DA and SPN subtype (Ref. 10; incorporated by reference in its entirety). Rather than being briefly stimulated by burst spiking of DA neurons, DIRs in the LID model are stimulated for long periods of time; this abnormally sustained stimulation is likely to underlie both the synaptic and biochemical signature of LID in dSPNs. This is what is seen in ex vivo brain slices shortly after the last dose of L-DOPA when striatal DA is high and DA receptor stimulation sustained (i.e. 'ON-state') (Ref. 10; incorporated by reference in its entirety). If mice are sacrificed later, when the effects of L-DOPA have waned and DA levels are low (i.e. 'OFF-state'), our results show that iSPNs are biased toward LTP induction because of reduced D2R signaling and elevated A2aR signaling (Refs. 22-24; incorporated by reference in their entireties). In this state, upregulation of iSPN GluN2B-enriched NMDARs promote the generation of AMPA-deficient silent synapses (FIG. 2), which provides an ideal substrate for activity-dependent potentiation of corticostriatal glutamatergic synapses, therefore promoting LID behaviors.

Previous studies in this field have not been able to systemically compare synaptic adaptations between the different striatal pathways at the different states of dyskinesia. All behavioral pharmacology studies performed thus far have been centered on the state where DA levels are high (ON-state), whereas most biochemical and electrophysiological studies have focused upon the changes in the state where DA levels are low (OFF-state). There is a real need for new strategies in studying the synaptic mechanisms governing the development of LID.

Experiments conducted during development of embodiments herein identified aberrant synaptic plasticity at glutamatergic synapses on striatal indirect pathway projection neurons as a causal agent in the induction of levodopa-induced dyskinesia (LID). Examination of the molecular determinants of this aberrant plasticity revealed it was linked to elevated activity in adenosine A2a receptors specifically during a period of time after levodopa administration.

Figure 3:
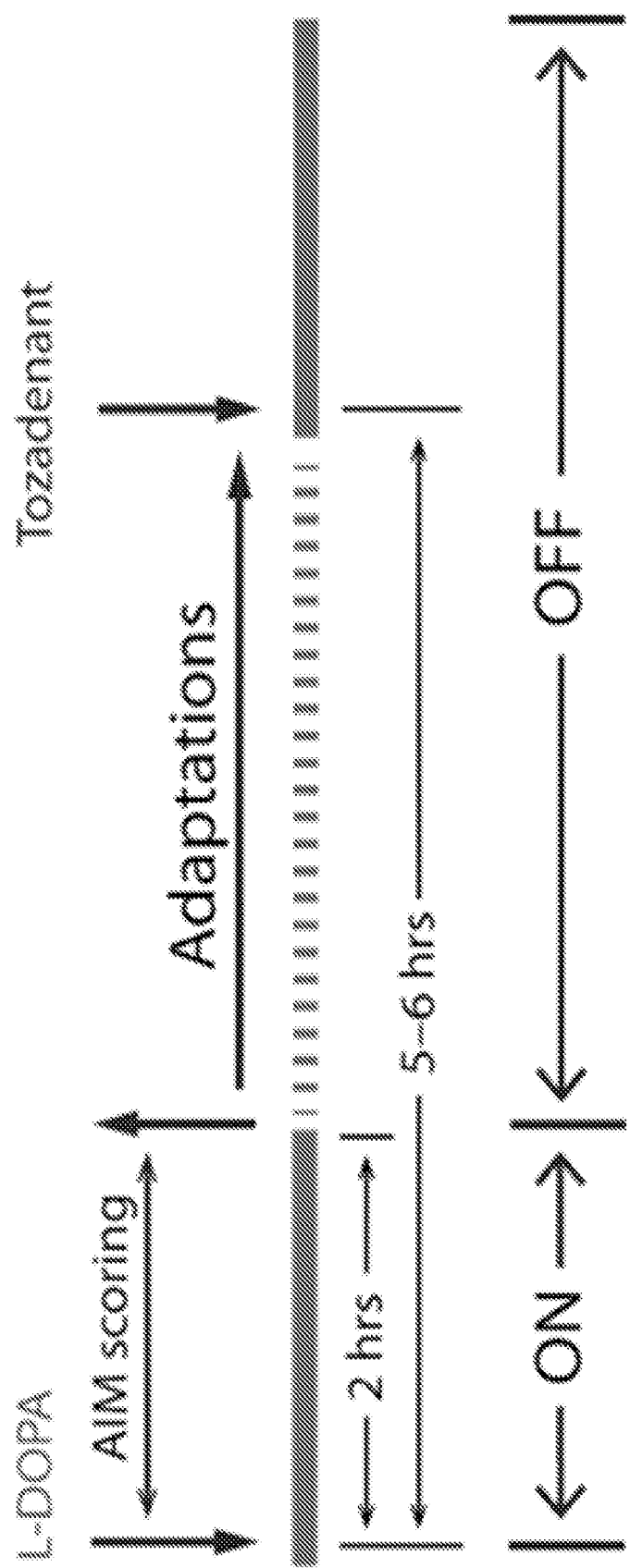
FIG. 3. Experimental timeline. Tozadenant is given 5-6 hours after L-DOPA doses.
Figure 4:
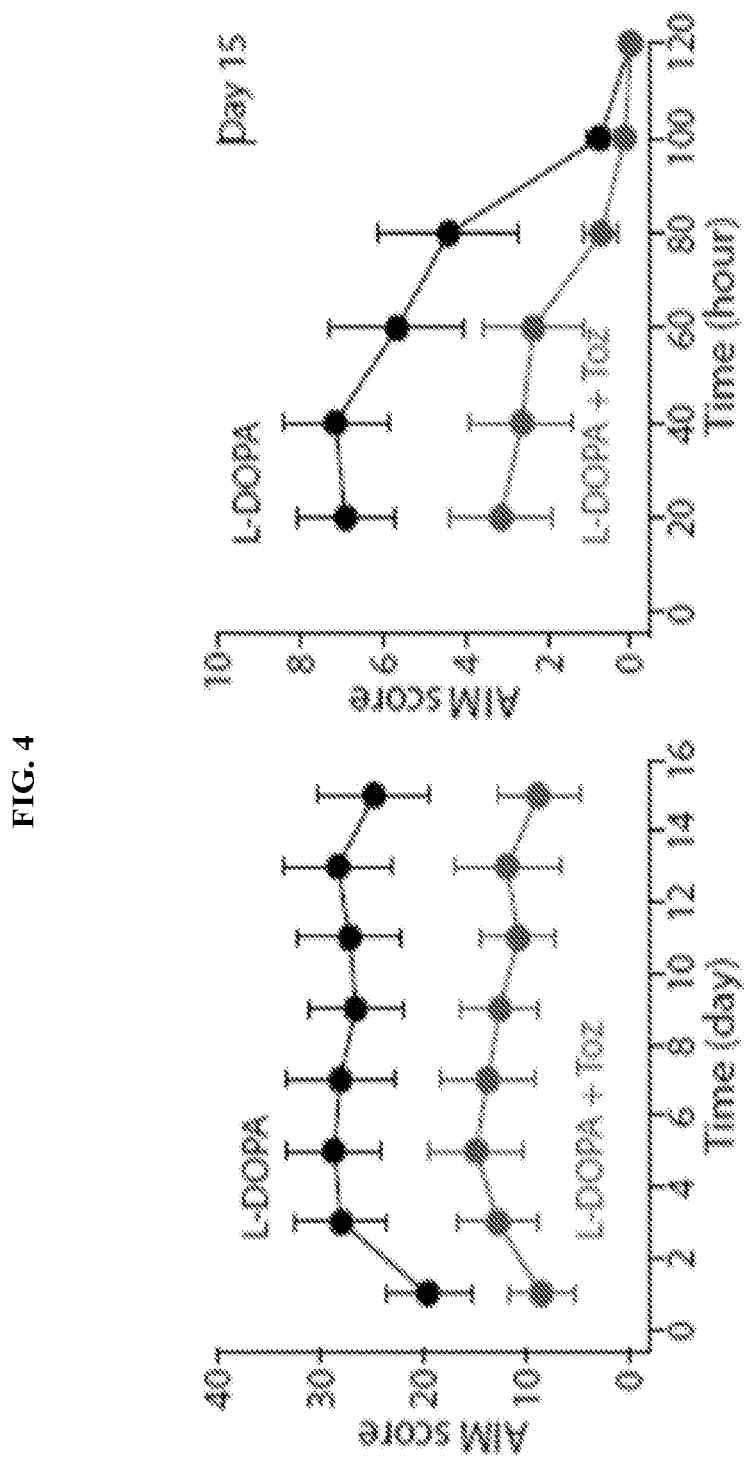
FIG. 4. The A2aR antagonist tozadenant attenuates the induction of LID. Left: systemic administration of tozadenant (Toz; 30 mg/kg) 5 hours after L-DOPA doses reduces the development of LID behaviors (L-DOPA+vehicle n=6; L-DOPA+Toz n=7; $p<0.05$). Right: plot of sum of AIM scores as a function of time measured on the day 15 ($p<0.05$).

An example of the complexity in dyskinesia can be illustrated by the experience with A2aR antagonists. A2aRs are primarily localized on iSPNs and couple to the same second messenger cascade as D1Rs and functionally oppose D2R signaling. In iSPNs, $G_{olf}$-coupled A2aRs are necessary for the induction of LTP. A2aR signaling also disrupts D2R-dependent induction of LTD (Ref. 17; incorporated by reference in its entirety). Thus, antagonism of A2aR signaling does not just blunt LTP induction but it enhances D2R-dependent eCB-LTD as well (Refs. 17, 25; incorporated by reference in their entireties). In dyskinetic mice shortly after the last L-DOPA dose, D2R-dependent iSPN LTD promotes LID behaviors (Ref. 10; incorporated by reference in its entirety). Therefore, co-administration of L-DOPA and an A2aR antagonist, like istradefylline (which enhances D2R signaling), in the ON-state should exacerbate, not attenuate, LID (Refs. 26-28: incorporated by reference in their entireties). Indeed, A2aR antagonists have failed in clinical trials when administered in this way. But, this is not how an A2aR antagonist should be administered to diminish aberrant synaptic plasticity. Rather, administration of A2aR antagonists (such as tozadenant and preladenant) in the OFF-state (FIG. 3), when A2aR signaling is high (refs 22-24; incorporated by reference in their entireties), attenuate aberrant LTP induction in iSPNs and in so doing ameliorate LID. Experiments conducted during development of embodiments herein have revealed that tozadenant treated in the LID OFF-state significantly attenuates LID scores induced by subsequent doses of L-DOPA (i.e., ON-state) (FIG. 4).

Experiments conducted during development of embodiments herein demonstrate that systemic administration of an A2a receptor antagonist at an interval after levodopa administration, when the effects of levodopa had begun to wain (the so-called 'off-state'), leads to effective attenuation of dyskinetic behavior with subsequent levodopa administration. The effectiveness of this 'delayed delivery' protocol stands in stark contrast to that seen with co-administration of levodopa and an A2a receptor antagonist in previous, failed clinical trials.

Materials and Methods

Mouse Unilateral 6-Hydroxydopamine (6-OHDA) Model and LID

Mice were anaesthetized with an isoflurane precision vaporizer, placed in a stereotaxic frame, and a hole was drilled over the medial forebrain bundle. After exposing the skull, 3.5 mg ml$^{-1}$ free base 6-OHDA with 0.02% ascorbic acid was injected using a glass micropipette. Three weeks after surgery, the degree of damage to nigrostriatal DA neurons was assessed with a forelimb-use asymmetry test. Striatal sections from a subset of mice were stained with tyrosine hydroxylase to verify successful lesion. One day after the test, mice underwent behavioral testing for abnormal involuntary movements (AIMs) following L-DOPA treatment. Treatment with L-DOPA was given daily for 15 days at the doses of 3 mg kg$^{-1}$. Animals were randomly allocated to receive treatment with L-DOPA and vehicle, or L-DOPA and an A2a receptor antagonist.

Patch-Clamp Recording

Mice were deeply anesthetized intraperitoneally with a mixture of ketamine and xylazine. Parasagittal slices were cut in ice-cold aCSF. Whole-cell and perforated-patch recordings were performed in the dorsolateral striatum at 30-31° C. Long-lasting synaptic plasticity was induced using protocols consisting of subthreshold synaptic stimulation paired with somatically induced action potentials (APs) at theta frequency (5 Hz). These protocols consisted of 20-60 trains of five bursts repeated at 0.1 Hz, with each burst composed of three APs preceded with three EPSPs at 50 Hz (pre-post timing pairing, +5 ms) or three APs followed by one EPSP (post-pre timing pairing, −10 ms). To ensure induction of consistent synaptic plasticity, postsynaptic neurons were depolarized to −70 mV from their typical resting membrane potentials (−85 mV) during their induction. $GABA_A$ was blocked by the bath application of gabazine (10 µM).

Optogenetic Stimulation

To stimulate channelrhodopsin-2 (ChR2)-expressing axons, a whole-field blue LED was used.

Data Analysis and Statistics Methods

Data analysis was conducted with Igor Pro 6 and Clampfit 9. EPSP amplitude was calculated from 50 sweeps immediately before the start of induction and 20-30 min after the end of induction. Compiled data were expressed as mean±SEM. Statistical tests were performed using Excel and SigmaStat. Nonparametric Mann-Whitney or Wilcoxon tests were used to assess the experiment results, using a probability threshold of 0.05. Statistical analyses for behavioral data were carried out using Prism 6. Data were analyzed using parametric repeated measure two-way ANOVA followed by post hoc Bonferroni's test.

All publications and patents mentioned above and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references, some of which are cited above, are herein incorporated by reference in their entireties.

1. Findley, L. J. The economic impact of Parkinson's disease. Parkinsonism Relat Disord 13 Suppl, S8-S12 (2007).
2. de Lau, L. M. L. et al. Incidence of parkinsonism and Parkinson disease in a general population: the Rotterdam Study. Neurology 63, 1240-1244 (2004).
3. Hornykiewicz, O. Dopamine (3-hydroxytyramine) and brain function. Pharmacol Rev 18, 925-964 (1966).
4. Kish, S. J., Shannak, K. & Hornykiewicz, O. Uneven pattern of dopamine loss in the striatum of patients with idiopathic Parkinson's disease. Pathophysiologic and clinical implications. N Engl J Med 318, 876-880 (1988).
5. Fahn, S. The history of dopamine and levodopa in the treatment of Parkinson's disease. Mov Disord 23 Suppl 3, S497-508 (2008).

6. Huot, P., Johnston, T. H., Koprich, J. B., Fox, S. H. & Brotchie, J. M. The pharmacology of L-DOPA-induced dyskinesia in Parkinson's disease. Pharmacol Rev 65, 171-222 (2013).
7. Gerfen, C. R. & Surmeier, D. J. Modulation of striatal projection systems by dopamine. Annu Rev Neurosci 34, 441-466 (2011).
8. Kreitzer, A. C. & Malenka, R. C. Striatal plasticity and basal ganglia circuit function. Neuron 60, 543-554 (2008).
9. Lerner, T. N. & Kreitzer, A. C. RGS4 is required for dopaminergic control of striatal LTD and susceptibility to parkinsonian motor deficits. Neuron 73, 347-359 (2012).
10. Shen, W. et al. M4 muscarinic receptor signaling ameliorates striatal plasticity deficits in models of L-DOPA-induced dyskinesia. Neuron 88, 762-773 (2015).
11. Bateup, H. S. et al. Distinct subclasses of medium spiny neurons differentially regulate striatal motor behaviors. Proc Natl Acad Sci USA 107, 14845-14850 (2010).
12. Fino, E., Glowinski, J. & Venance, L. Bidirectional activity-dependent plasticity at corticostriatal synapses. J Neurosci 25, 11279-11287 (2005).
13. Jia, Y., Gall, C. M. & Lynch, G. Presynaptic BDNF promotes postsynaptic long-term potentiation in the dorsal striatum. J Neurosci 30, 14440-14445 (2010).
14. Kerr, J. N. & Wickens, J. R. Dopamine D-1/D-5 receptor activation is required for long-term potentiation in the rat neostriatum in vitro. J Neurophysiol 85, 117-124 (2001).
15. Pawlak, V. & Kerr, J. N. D. Dopamine receptor activation is required for corticostriatal spike-timing-dependent plasticity. J Neurosci 28, 2435-2446 (2008).
16. Plotkin, J. L. et al. Impaired TrkB receptor signaling underlies corticostriatal dysfunction in Huntington's disease. Neuron 83, 178-188 (2014).
17. Shen, W., Flajolet, M., Greengard, P. & Surmeier, D. J. Dichotomous dopaminergic control of striatal synaptic plasticity. Science 321, 848-851 (2008).
18. Yagishita, S. et al. A critical time window for dopamine actions on the structural plasticity of dendritic spines. Science 345, 1616-1620 (2014).
19. Park, H., Popescu, A. & Poo, M.-M. Essential role of presynaptic NMDA receptors in activity-dependent BDNF secretion and corticostriatal LTP. Neuron 84, 1009-1022 (2014).
20. Pascoli, V., Turiault, M. & Lüscher, C. Reversal of cocaine-evoked synaptic potentiation resets drug-induced adaptive behaviour. Nature 481, 71-75 (2011).
21. Picconi, B. et al. Loss of bidirectional striatal synaptic plasticity in L-DOPA-induced dyskinesia. Nat Neurosci 6, 501-506 (2003).
22. Calon, F. et al. Increased adenosine A2A receptors in the brain of Parkinson's disease patients with dyskinesias. Brain 127, 1075-1084 (2004).
23. Mishina, M. et al. Adenosine A(2A) receptors measured with [C]TMSX PET in the striata of Parkinson's disease patients. PLoS ONE 6, e17338 (2011).
24. Tomiyama, M. et al. Upregulation of striatal adenosine A2A receptor mRNA in 6-hydroxydopamine-lesioned rats intermittently treated with L-DOPA. Synapse 52, 218-222 (2004).
25. Lerner, T. N., Home, E. A., Stella, N. & Kreitzer, A. C. Endocannabinoid signaling mediates psychomotor activation by adenosine A2A antagonists. J Neurosci 30, 2160-2164 (2010).
26. Chen, W., Wang, H., Wei, H., Gu, S. & Wei, H. Istradefylline, an adenosine $A_2A$ receptor antagonist, for patients with Parkinson's Disease: a meta-analysis. J. Neurol. Sci. 324, 21-28 (2013).
27. Kondo, T., Mizuno, Y. Japanese Istradefylline Study Group. A long-term study of istradefylline safety and efficacy in patients with Parkinson disease. Clin Neuropharmacol 38, 41-46 (2015).
28. Lundblad, M., Vaudano, E. & Cenci, M. A. Cellular and behavioural effects of the adenosine A2a receptor antagonist KW-6002 in a rat model of 1-DOPA-induced dyskinesia. J Neurochem 84, 1398-1410 (2003).
29. Hauser, R. A. et al. Preladenant in patients with Parkinson's disease and motor fluctuations: a phase 2, double-blind, randomised trial. Lancet Neurol 10, 221-229 (2011).
30. Park, A. & Stacy, M. Istradefylline for the treatment of Parkinson's disease. Expert Opin Pharmacother 13, 111-114 (2012).
31. Chen, W., Wang, H., Wei, H., Gu, S. & Wei, H. Istradefylline, an adenosine $A_2A$ receptor antagonist, for patients with Parkinson's Disease: a meta-analysis. J. Neurol. Sci. 324, 21-28 (2013).
32. Mizuno, Y. et al. Clinical efficacy of istradefylline (KW-6002) in Parkinson's disease: a randomized, controlled study. Mov Disord 25, 1437-1443 (2010).
33. Fernandez, H. H. et al. Istradefylline as monotherapy for Parkinson disease: results of the 6002-US-051 trial. Parkinsonism Relat Disord 16, 16-20 (2010).
34. LeWitt, P. A. et al. Adenosine A2A receptor antagonist istradefylline (KW-6002) reduces 'off' time in Parkinson's disease: a double-blind, randomized, multicenter clinical trial (6002-US-005). Ann Neurol 63, 295-302 (2008).
35. Hauser, R. A. et al. Tozadenant (SYN115) in patients with Parkinson's disease who have motor fluctuations on levodopa: a phase 2b, double-blind, randomised trial. Lancet Neurol 13, 767-776 (2014).

The invention claimed is:

1. A method for the treatment of a neurodegenerative disorder with reduced dykinesia, comprising:
   (a) administering to a subject a dose of levodopa at a first time-point;
   (b) administering to the subject a dose of an A2a antagonist at a second time-point following a time delay of at least 2 hours from the first time point, wherein the A2a antagonist is not caffeine.

2. A method for the treatment of a neurodegenerative disorder with reduced levodopa-induced dykinesia, comprising administering to the subject a dose of an A2a antagonist at a time when plasma levodopa levels are low.

3. The method of claim 1, wherein the neurodegenerative disorder is Parkinson's disease.

4. The method of claim 1, wherein the A2a antagonist is selected form the group consisting of: ATL-444, Istradefylline (KW-6002), MSX-3, Preladenant (SCH-420,814), SCH-58261, SCH-412,348, SCH-442,416, ST-1535, VER-6623, VER-6947, VER-7835, Vipadenant (BIIB-014) ZM-241,385, Tozadenant, V81444 and CPI-444.

5. The method of claim 1, wherein the second time-point is after symptom-reduction effects of the dose of levodopa have begun to decrease.

6. The method of claim 1, further comprising co-administering an additional therapeutic agent for the treatment of the neurodegenerative disorder or symptom reduction.

7. The method of claim 6, wherein the additional therapeutic agent is selected from the list consisting of dopamine agonists, MAO-B inhibitor, amantadine, anticholinergics, quetiapine, cholinesterase inhibitors, modafinil, and nonsteroidal anti-inflammatory drugs.

8. The method of claim 6, wherein the additional therapeutic agent is administered at the first time-point.

9. The method of claim 6, wherein the additional therapeutic agent is administered at the second time-point.

* * * * *